United States Patent [19]

Burton et al.

[11] Patent Number: 5,071,834
[45] Date of Patent: Dec. 10, 1991

[54] PURIFIED ACTIVIN B COMPOSITION

[75] Inventors: Louis E. Burton, San Mateo; Anthony J. Mason; Charles H. Schmelzer, both of San Francisco, all of Calif.

[73] Assignee: Genentech, Inc., South San Francisco, Calif.

[21] Appl. No.: 597,293

[22] Filed: Oct. 12, 1990

[51] Int. Cl.$^5$ .................... A61K 37/02; A61K 37/43
[52] U.S. Cl. ........................................ 514/12; 514/8; 514/21; 530/399
[58] Field of Search ................ 514/8, 21, 12; 530/399

[56] References Cited

U.S. PATENT DOCUMENTS 4,879,226  11/1989  Wallace et al. .

FOREIGN PATENT DOCUMENTS 0210461  2/1987  European Pat. Off. .
0210461  2/1987  European Pat. Off. .
0222491  5/1987  European Pat. Off. .
WO86/06076  10/1986  PCT Int'l Appl. .

OTHER PUBLICATIONS

Mason, T., "Nonsteroidal Gonadal Factors: Physiological Roles and Possibilities in Contraceptive Development", Hodgen et al., Eds., Jones Institute Press, Norfolk, Va., pp. 19-29 (1988).

Mason et al., Biochem. Biophys. Res. Commun. 135 (3):957-964 (1986).

Mason et al., "Inhibin-Non-Steroidal Regulation of Follicle Stimulating Hormone Secretion", Serono Symposia Publications from Raven Press, vol. 42, pp. 77-88 (1987).

Eto et al., Biochem. Biophys. Res. Commun, 142 (3):1095-1103 (1987).

Murata et al., Proc. Natl. Acad. Sci. U.S.A. 85:2434-2438 (1988).

Yu et al., Nature 330:765-767 (1987).

Ikawa et al., Gann 66:583-584 (1975).

Murata et al., Biochem. Biophys. Res. Commun. 151 (1):230-235 (1988).

Mason et al., Molecular Endocrinology, 3:1352-1358 (1989).

Primary Examiner—Howard E. Schain
Assistant Examiner—Choon P. Koh
Attorney, Agent, or Firm—Janet E. Hasak

[57] ABSTRACT

A pharmaceutical composition and method are provided for erythropoietin therapy, such as treatment of an anemic disease, wherein an effective amount of activin with two beta$_B$ chains formulated in a pharmaceutically acceptable carrier is administered to a patient or animal in need of such therapy. Preferably the activin is human and the composition is administered parenterally.

6 Claims, 18 Drawing Sheets

Fig.6A.

```
1   TGCTCCCTGACAGCCACAACCTTACAGCACTGACTGCATTCAGAGGAACCTGCAAACAAACTTTTGTCTTGTTCCAGAGAATT
101 TGCTGAAGAGAGGAGGAGAAAAAACCAAAAAAAAAATAAAAAAATCCACACACAAAAACCTGCGGTGAGGGGGAGGAAAAGCAGGCCT
                                                                            -28  -20
                                                                            Met Pro Leu Leu Trp Leu Arg Gly Phe Leu Leu Ala Ser Cys Trp
201 TTTAAAAGGCAATCACAACAACTTTTGCTGCCAGG                                     ATG CCC TTG CTT TGG CTG AGA GGA TTT CTG TTG GCA AGT TGC TGG
       -10                                           -1  +1                                                    10
    Ile Ile Val Arg Ser Ser Pro Thr Pro Gly Ser Glu Gly His Ser Ala Ala Pro Asp Cys Pro Ser Cys Ala Leu
282 ATT ATA GTG AGG AGT TCC CCC ACC CCA GGA TCC GAG CAC AGC GCG GCC CCC GAC TGT CCG TCC TGT GCG CTG
                                        20                                        30
    Ala Ala Leu Pro Lys Asp Val Pro Asn Ser Gln Pro Glu Met Val Glu Ala Val Lys Lys His Ile Leu Asn Met
357 GCC GCC CTC CCA AAG GAT GTA CCC AAC TCT CAG CCA GAG ATG GTG GAG GCC GTC AAG AAG CAC ATT TTA AAC ATG
             40                                          50                                        60
    Leu His Leu Lys Lys Arg Pro Asp Val Thr Gln Pro Val Pro Lys Ala Ala Leu Leu Asn Ala Ile Arg Lys Leu
432 CTG CAC TTG AAG AAG AGA CCC GAT GTC ACC CAG CCG GTA CCC AAG GCG GCG CTT CTG AAC GCC ATC AGA AAG CTT
                                      70                                          80
    His Val Gly Lys Val Gly Glu Asn Gly Tyr Val Glu Ile Glu Asp Asp Ile Gly Arg Arg Ala Glu Met Asn Glu
507 CAT GTG GGC AAA GTC GGG GAG AAC GGG TAT GTG GAG ATA GAG GAT GAC ATT GGA AGG AGG GCA GAA ATG AAT GAA
              90                                       100                                       110
    Leu Met Glu Gln Thr Ser Glu Ile Ile Thr Phe Ala Glu Ser Gly Thr Ala Arg Lys Thr Leu His Phe Glu Ile
582 CTT ATG GAG CAG ACC TCG GAG ATC ATC ACG TTT GCC GAG TCA GGA ACA GCC AGG AAG ACG CTG CAC TTC GAG ATT
```

Fig.6B.

```
                                                                                    120                                                       130
     Ser Lys Glu Gly Ser Asp Leu Ser Val Val Glu Arg Ala Glu Val Trp Leu Phe Leu Lys Val Pro Lys Ala Asn
657  TCC AAG GAA GGC AGT GAC CTG TCA GTG GTG GAG CGT GCA GAA GTC TGG CTC TTC CTA AAA GTC CCC AAG GCC AAC
                     140                                                       150                                                       160
     Arg Thr Arg Thr Lys Val Thr Ile Arg Leu Phe Gln Gln Lys His Pro Gln Gly Ser Leu Asp Ala Thr Gly Glu
732  AGG ACC AGG ACC AAA GTC ACC ATC CGC CTC TTC CAG CAG AAG CAC CCG CAG GGC AGC TTG GAC GCA ACA GGG GAA
                                                           170                                                       180
     Glu Ala Glu Glu Val Gly Leu Lys Gly Glu Arg Ser Ser Glu Leu Leu Ser Lys Val Val Asp Ala Arg Lys
807  GAG GCC GAG GAG GTG GGA CTT AAG GGG GAG AGG AGT AGT GAA CTG CTG TTG TCT CTC AAA GTA GTA GAC GCT CGG AAG
                     190                                                       200                                                       210
     Ser Thr Trp His Val Phe Pro Val Ser Ser Ser Ile Gln Arg Leu Leu Asp Gln Gly Lys Ser Ser Leu Asp Val
882  AGC ACC TGG CAT GTC TTC CCT GTC TCC AGC AGC ATC CAG CGG TTG CTG GAC CAG CAG GGC AAG AGC TCC CTG GAC GTT
                                                           220                                                       230
     Arg Ile Ala |Lys Cys| Gln Glu Ser Gly Ala Ser Leu Val Leu Leu Gly Lys Lys Lys Lys Lys Glu Glu
957  CGG ATT GCC |AAG TGT| CAG GAG AGT GGC GCC AGC TTG GTT CTC CTG GGC AAG AAG AAG AAG AAG GAA GAG
                     240                                                       250                                                       260
     Glu Gly Glu Gly Lys Gly Gly Gly Gly Glu Gly Ala Asp Glu Lys Glu Gln Ser His Arg
1032 GAG GGA GAA GGG AAA GGG GGT GGA GGA GCA GAT GAA AAG GAA CAG TCG CAC AGA
```

Fig.6C.

→ β_A subunit

```
       Pro Phe Leu Met Leu Gln Ala Arg Gln Ser Glu Asp His Pro His Arg Arg Arg Gly Leu Glu Cys Asp
1107   CCT TTC CTC ATG CTG CAG GCC CGG CAG TCT GAA GAC CAC CCT CAT CGC CGT CGG GGC TTG GAG TGT GAT
                                     270                300                    310

Gly Lys Val Asn Ile Cys Cys Lys Lys Gln Phe Phe Val Ser Phe Lys Asp Ile Gly Trp Asn Asp Trp Ile Ile
1182   GGC AAG GTC AAC ATC TGC TGT AAA CAG TTC TTT GTC AGT TTC AAG GAC ATC GGC TGG AAT GAC TGG ATC ATT
                       290                                       320                        330

Ala Pro Ser Gly Tyr His Ala Asn Tyr Cys Glu Gly Glu Cys Pro Ser His Ile Ala Gly Thr Ser Gly Ser Ser
1257   GCT CCC TCT GGC TAT CAT GCC AAC TAC TGC GAG GGT GAG CCG AGC CAT ATA GCA GGC ACG TCC GGG TCC TCA
                340                                       350                        360

Leu Ser Phe His Ser Thr Val Ile Asn His Tyr Arg Met Arg Gly His Ser Pro Phe Ala Asn Leu Lys Ser Cys
1332   CTG TCC TTC CAC TCA ACA GTC ATC AAC CAC TAC CGC ATG CGG GGC CAT AGC CCC TTT GCC AAC CTC AAA TCG TGC
                                            370                            380

Cys Val Pro Thr Lys Leu Arg Pro Met Ser Met Leu Tyr Tyr Asp Asp Gly Gln Asn Ile Ile Lys Lys Asp Ile
1407   TGT GTG CCC ACC AAG CTG AGA CCC ATG TCC ATG TTG TAC TAT GAT GAT GGT CAA AAC ATC ATC AAA AAG GAC ATT
                           390                                                     398

Gln Asn Met Ile Val Glu Glu Cys Gly Cys Ser AM*
1482   CAG AAC ATG ATC GTG GAG GAG TGT GGG TGC TCA TAG AGTTGCCCAGCCCAGGGGGAAAGGGAGCAAGAGTTGTCCAGAGAAGACAGTG

1570   GCAAAATGAAGAATTTTTAAGGTTTCTGAGTTAACCAGAAATAGAAAAAACAAAACA polyA
```

Fig. 7A.

```
                                                                    NcoI
                                                                   ┌─ 1 ─┐
                                                                   Met Asp
  1   CTCGACTCGGCTCGCCTCGCGGCGGGCGCCCTCGTCGCCAGCGGCGCACC ATG GAC

10
        Gly Leu Pro Gly Arg Ala Leu Gly Ala Ala Cys Leu Leu Leu Leu
 57     GGG CTG CCC GGT CGG GCG CTG GGG GCC GCC TGC CTT CTG CTG CTG

20 ↓                                              30
        Ala Ala Gly Trp Leu Gly Pro Glu Ala Trp Gly Ser Pro Thr Pro
102     GCG GCC GGC TGG CTG GGG CCT GAG GCC TGG GGC TCA CCC ACG CCC

40
        Pro Pro Thr Pro Ala Ala Pro Pro Pro Pro Pro Pro Pro Gly Ser
147     CCG CCG ACG CCT GCC GCG CCG CCG CCA CCC CCG CCA CCC GGA TCC 50                                                60
        Pro Gly Gly Ser Gln Asp Thr Cys  Thr Ser Cys  Gly Gly Phe Arg
192     CCG GGT GGC TCG CAG GAC ACC TGT  ACG TCG TGC  GGC GGC TTC CGG

70
        Arg Pro Glu Glu Leu Gly Arg Val Asp Gly Asp Phe Leu Glu Ala
237     CGG CCA GAG GAG CTC GGC CGA GTG GAC GGC GAC TTC CTG GAG GCG 80                                                90
        Val Lys Arg His Ile Leu Ser Arg Leu Gln Met Arg Gly Arg Pro
282     GTG AAG CGG CAC ATC TTG AGC CGC CTG GAG ATG CGG GGC CGG CCC
                                            └─────┘
                                              PstI

┌───────┐                       100
        Asn Ile Thr His Ala Val Pro Lys Ala Ala Met Val Thr Ala Leu
327     AAC ATC ACG CAC GCC GTG CCT AAG GCC ACC ATG GTC ACG GCC CTG 110                                         120
        Arg Lys Leu His Ala Gly Lys Val Arg Glu Asp Gly Arg Val Glu
372     CGC AAG CTG CAC GCG GGC AAG GTG CGC GAG GAC GGC CGC GTG GAG

130
        Ile Pro His Leu Asp Gly His Ala Ser Pro Gly Ala Asp Gly Gln
417     ATC CCG CAC CTC GAC GGC CAC GCC AGC CCG GGC GCC GAC GGC CAG
```

Fig. 7B.

```
                    140                                          150
       Glu Arg Val Ser Glu Ile Ile Ser Phe Ala Glu Thr Asp Gly Leu
462    GAG CGC GTT TCC GAA ATC ATC AGC TTC GCC GAG ACA GAT GGC CTC

160
       Ala Ser Ser Arg Val Arg Leu Tyr Phe Phe Ile Ser Asn Glu Gly
507    GCC TCC TCC CGG GTC CGC CTA TAC TTC TTC ATC TCC AAC GAA GGC 170                                          180
       Asn Gln Asn Leu Phe Val Val Gln Ala Ser Leu Trp Leu Tyr Leu
552    AAC CAG AAC CTG TTT GTG GTC CAG GCC AGC CTG TGG CTT TAC CTG

190
       Lys Leu Leu Pro Tyr Val Leu Glu Lys Gly Ser Arg Arg Lys Val
597    AAA CTC CTG CCC TAC GTC CTG GAG AAG GGC AGC CGG CGG AAG GTG 200                                          210
       Arg Val Lys Val Tyr Phe Gln Glu Gln Gly His Gly Asp Arg Trp
642    CGG GTC AAA GTG TAC TTC CAG GAG CAG GGC CAC GGT GAC AGG TGG

220
       Asn Met Val Glu Lys Arg Val Asp Leu Lys Arg Ser Gly Trp His
687    AAC ATG GTG GAG AAG AGG GTG GAC CTC AAG CGC AGC GCC TGG CAT 230                                          240
       Thr Phe Pro Leu Thr Glu Ala Ile Gln Ala Leu Phe Glu Arg Gly
732    ACC TTC CCA CTC ACG GAG GCC ATC CAG GCC TTG TTT GAG CGG GGC

250
       Glu Arg Arg Leu Asn Leu Asp Val Gln Cys  Asp Ser Cys  Gln Glu
777    GAG CGG CGA CTC AAC CTA GAC GTG CAG TGT  GAC AGC TGC  CAG GAG 260                                          270
       Leu Ala Val Val Pro Val Phe Val Asp Pro Gly Glu Glu Ser His
822    CTG GCC GTG GTG CCG GTG TTC GTG GAC CCA GGC GAA GAG TCG CAC

280
       Arg Pro Phe Val Val Val Gln Ala Arg Leu Gly Asp Ser Arg His
867    CGG CCC TTT GTG GTG GTG CAG GCT CGG CTG GGC GAC AGC AGG CAC
```

Fig. 7C.

```
                290         ┌→ β_B subunit                    300
        Arg Ile Arg Lys Arg Gly Leu Glu [Cys] Asp Gly Arg Thr Asn Leu
   912  CGC ATT CGC AAG CGA GGC CTG GAG [TGC] GAT GCC CGG ACC AAC CTC 310
        [Cys Cys] Arg Gln Gln Phe Phe Ile Asp Phe Arg Leu Ile Gly Trp
   957  [TGT TGC] AGG CAA CAG TTC TTC ATT GAC TTC CGC CTC ATC GGC TGG 320                                 330
        Asn Asp Trp Ile Ile Ala Pro Thr Gly Tyr Tyr Gly Asn Tyr [Cys]
  1002  AAC GAC TGG ATC ATA GCA CCC ACC GGC TAC TAC GCG AAC TAC [TGT]

340
        Glu Gly Ser [Cys] Pro Ala Tyr Leu Ala Gly Val Pro Gly Ser Ala
  1047  GAG GGC AGC [TGC] CCA GCC TAC CTG GCA GGG GTC CCC GGC TCT GCC 350                                 360
        Ser Ser Phe His Thr Ala Val Val Asn Gln Tyr Arg Met Arg Gly
  1092  TCC TCC TTC CAC ACG GCT GTG GTG AAC CAG TAC CGC ATG CGG GGT

370
        Leu Asn Pro Gly Thr Val Asn Ser [Cys Cys] Ile Pro Thr Lys Leu
  1137  CTG AAC CCC AGC ACG GTG AAC TCC [TGC TGC] ATT CCC ACC AAG CTG 380                                 390
        Ser Thr Met Ser Met Leu Tyr Phe Asp Asp Glu Tyr Asn Ile Val
  1182  AGC ACC ATG TCC ATG CTG TAC TTC GAT GAT GAG TAC AAC ATC GTC 400                          407
        Lys Arg Asp Val Pro Asn Met Ile Val Glu Glu [Cys] Gly [Cys] Ala
  1227  AAG CGG GAC GTG CCC AAC ATG ATT GTG GAG GAG [TGC] GGC [TGC] GCC

OP*
  1272  TGA CAGTGCAAGCTTGGGGCACGGTGGTGGGGCACGGAGGGCAGTCCCGGGTGGGCTT
```

PURIFIED ACTIVIN B COMPOSITION

BACKGROUND OF THE INVENTION

This invention relates to a pharmaceutical composition and methods for treating erythropoietin disorders. More particularly, this invention is directed to methods for treating patients or animals in need of erythropoietin therapy using activin with two beta$_B$ chains.

Erythropoiesis, the production of red blood cells occurs continuously throughout the human life span to offset cell destruction. Erythropoiesis enables sufficient numbers of red blood cells to be available in the blood for proper tissue oxygenation, but not so many that the cells would impede circulation. The formation of red blood cells occurs in the bone marrow and is under the control of the hormone erythropoietin.

The amount of erythropoietin in circulating plasma increases when oxygen transport by blood cells in the circulation is reduced. This condition, called hypoxia, may be caused by large losses of blood as through hemorrhaging, radiation over-exposure that destroys red blood cells, reduction in oxygen intake due to high altitudes or prolonged unconsciousness, or various forms of anemia. Under conditions of hypoxia, erythropoietin increases the production of red blood cells by inducing the conversion of precursor cells in the bone marrow into proerythroblasts that subsequently mature, manufacture hemoglobin, and become released into the circulation as red blood cells. When the number of red blood cells in circulation is greater than needed for normal tissue oxygen requirements, the amount of erythropoietin in circulation decreases.

Many types of pharmaceuticals have been employed to relieve anemic conditions, depending on the cause. For example, iron preparations are employed generally for iron-deficiency anemia, vitamin $B_{12}$ and folic acid for malignant anemia, and adrenocortical steroids, such as corticoids, for hemolytic anemia. Steroid hormones are known to have powerful erythropoietic stimulating action and are regarded as effective medicines; however, such hormones exhibit strong side effects and are generally undesirable for administration over long time periods.

Recently, erythropoietin has been proposed as an effective drug for alleviating anemia. U.S. Pat. No. 4,703,008 issued Oct. 27, 1987 describes the recombinant production of erythropoietin for producing the drug in commercially viable quantities.

Activin, which was originally identified in a study of the hormone inhibin, subsequently isolated from ovaries, and found to have follicle stimulating hormone (FSH)-releasing activity, consists of a homodimer or heterodimer of inhibin $\beta$ subunits, which may be $\beta_A$ or $\beta_B$ subunits. There is 95–100% amino acid conservation of $\beta$ subunits among human, porcine, bovine, and rat activins. The $\beta_A$ and $\beta_B$ subunits within a given species are about 64–70% homologous. The activin $\beta_A\beta_A$ and $\beta_A\beta_B$ dimers have been identified in follicular fluid, and the former (hereafter "Activin A") has been cloned. Mason et al., *Biochem. Biophys. Res. Commun.*, 135: 957 (1986); EP Pub. No. 222,491 published May 20, 1987. The $\beta_B\beta_B$ form of activin (hereafter "Activin B") has not been isolated thus far from a natural source, but may be produced by recombinant techniques. The complete sequence of the $\beta_B$ subunit is published in Serono Symposium Publications, entitled "Inhibin- Non-Steroidal Regulation of Follicle Stimulating Hormone Secretion", eds. H. G. Burger et al., abstract by A. J. Mason et al., vol. 42, pp 77–88 (Raven Press, 1987), entitled "Human Inhibin and Activin: Structure and Recombinant Expression in Mammalian Cells."

Activin A has been found recently to have erythropoietic-stimulating activity as well as FSH-releasing activity. See EP Publ. No. 210,461 published Feb. 4, 1987 (where the protein is called BUF-3), Eto et al., *Biochem. Biophys. Res. Commun.* 142: 1095–1103 (1987) and Murata et al., *Proc. Natl. Acad. Sci.* U.S.A., 85: 2434–2438 (1988) (where the protein is called EDF), and Yu et al., *Nature*, 330: 765–767 (1987) (where the protein is called FRP). In addition, Yu et al. found that the addition of Activin A significantly enhanced the formation of erythroid colony-forming units in the presence of erythropoietin up to 300%, but alone did not promote colony formation.

It is an object of the present invention to provide a method for treating erythropoietic disorders using a pharmaceutical composition encompassing Activin B.

Another object of the invention is to minimize the need for transfusion therapy, thereby reducing the chances of transmission of infectious agents.

These and other objects will become apparent to one of ordinary skill in the appropriate art.

SUMMARY OF THE INVENTION

These objects are achieved by providing a composition comprising at least about 80% by weight of human Activin B, the remaining percentage, if any, being polypeptide(s) of human origin.

In another aspect, this invention provides a pharmaceutical composition useful for erythropoietin therapy comprising an effective amount of Activin B formulated in a pharmaceutically acceptable carrier.

In a further embodiment, the pharmaceutical composition additionally comprises a compound selected from the group consisting of an iron preparation, vitamin $B_{12}$, folic acid, an adrenocortical steroid, an erythropoietin, a testosterone, a progenitor cell stimulator, insulin-like growth factor, a prostaglandin, serotonin, cyclic AMP, prolactin, triiodothyzonine, methenolene, stanozolol, nandrolone, an adrenergic agonist, a thyroid hormone, an androgen, a hepatic erythropoietic factor, an erythrotropin, and an erythrogenin.

In another aspect, this invention relates to a method comprising administering to a patient or animal in need of erythropoietin therapy an effective amount of the pharmaceutical composition or its variants.

BRIEF DESCRIPTION OF THE DRAWINGS

FIG. 6A, 6B, & 6C depicts the nucleotide sequence and deduced amino acid sequence of the human $\beta_A$ inhibin cDNA.

FIG. 7A, 7B, & 7C the deduced nucleotide and deduced amino acid sequence of human $\beta_B$ inhibin cDNA, including the restriction sites for the genomic insert. The cysteine residues are shown in boxes.

DESCRIPTION OF THE PREFERRED EMBODIMENTS

Figure 1A:
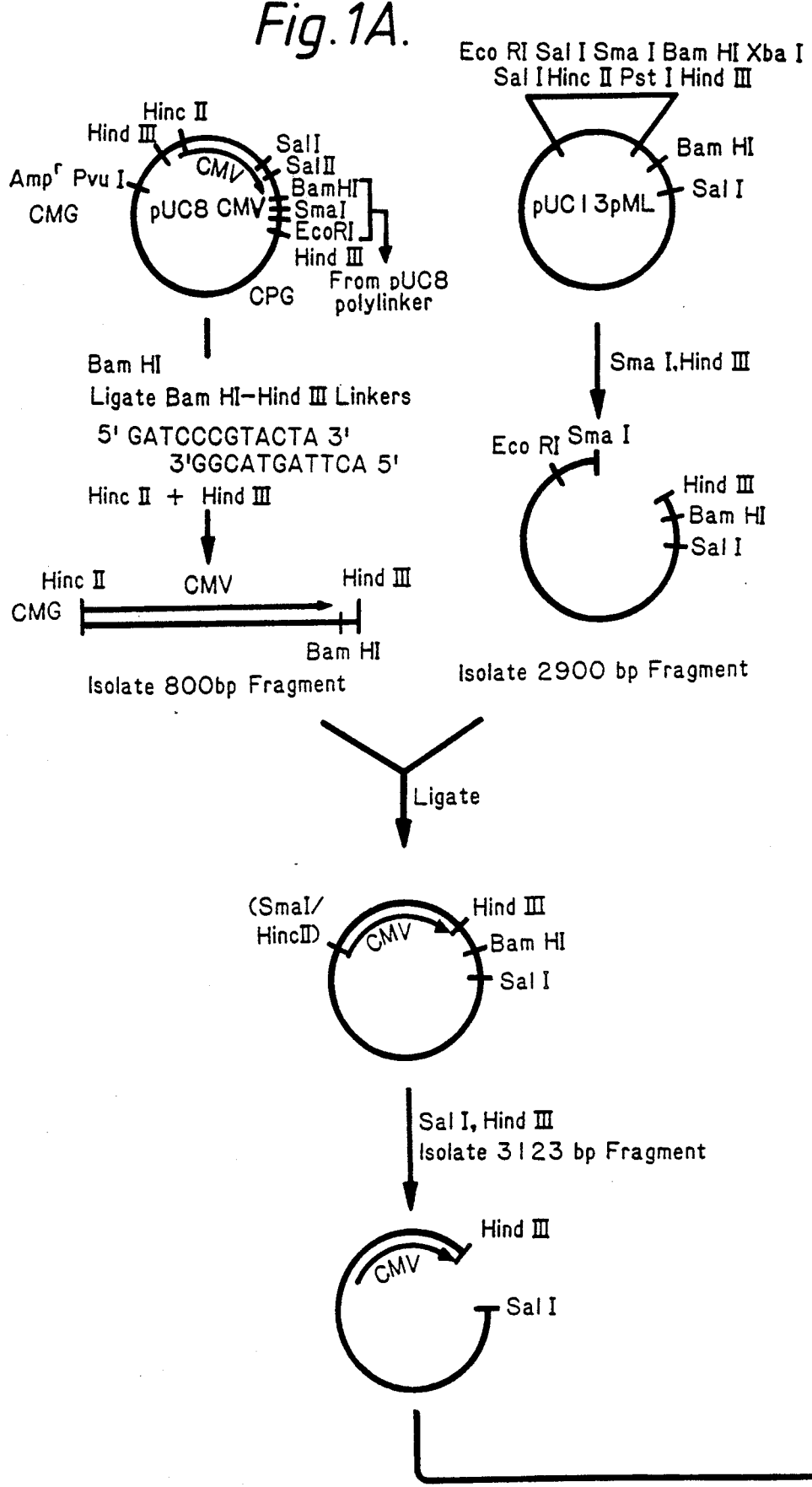
FIG. 1A, 1B, & 1C depicts the construction of the starting expression vector pF8CIS used to construct the ultimate expression vector for producing human Activin B.

For purposes herein, the term "erythropoietin therapy" refers to therapy having as its objective the supplementation of the oxygen-carrying capacity of blood. Examples include the treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in mammals. Included within this class of humans treatable with the Activin B are patients generally requiring blood transfusions and including trauma victims, surgical patients, renal disease patients including dialysis patients, and patients with a variety of blood composition-affecting disorders, such as hemophilia, cystic fibrosis, pregnancy, menstrual disorders, early anemia of prematurity, spinal cord injury, space flight, acute blood loss, aging, and various neoplastic disease states accompanied by abnormal erythropoiesis, physiologic anemias, and the like. In addition, erythropoietin therapy includes the enhancement of the oxygen-carrying capacity of individuals encountering hypoxic environmental conditions.

The term "Activin B" refers to the homodimer of activin with two beta$_B$ chains ($\beta_B\beta_B$) with the sequence shown in FIG. 7, the alleles of these activin chains, and predetermined mutations thereof. Generally, amino acid sequence variables (including amino acid insertions, substitutions, and deletions) have an amino acid sequence with at least about 80% homology, and more typically at least 90% homology, to the sequence of Activin B shown in FIG. 7, so long as they are effective in the method described herein. Henceforth, the term "Activin B" shall mean either the native sequence or variant form unless otherwise appropriate.

It is within the scope hereof to employ Activin B from animals other than humans, for example, porcine or bovine sources, to treat humans. For example, the nucleotide and deduced amino acid sequences of the porcine inhibin $\beta_B$ chain are found in FIGS. 2A and 2B of EP 222,491, supra, the disclosure of which is incorporated herein by reference. Likewise, if it is desirable to treat other mammalian species such as domestic and farm animals and sports or pet animals, human Activin B, as well as Activin B from other species, is suitably employed. Thus, for example, uremic sheep can be treated using a therapeutic regimen comprising human Activin B based on in vivo response to erythropoietin-rich plasma infusions. See Eschbach et al., *J. Clin. Invest.* 74: 434 (1984) for EPO treatment of induced hypoproliferative anemia associated with chronic renal failure in sheep.

The human Activin B composition provided herein is purified to the extent of at least about 80% by weight human Activin B, with the remaining polypeptide(s), if any, being of human, not animal, origin. More preferably, the composition comprises at least about 90% by weight human Activin B, and most preferably at least about 95%, with the remaining polypeptide(s), if any, being of human origin. The purity of the composition is suitably assayed visually from a stained SDS-PAGE non-reducing gel. For example, a known amount of the Activin B sample (e.g., 5–15 μg) is run on a non-reducing SDS-PAGE gel, the gel is stained with Coomassie Blue stain, and the lane is scanned. If only one protein band is present, one can estimate that the sample contains at least 95% by weight Activin B.

The Activin B is administered to the patient by any suitable technique, including parenteral, sublingual, topical, intrapulmonary, and intranasal administration. The specific route of administration will depend, e.g., on the type of erythropoietic therapy required. Examples of parenteral administration include intramuscular, subcutaneous, intravenous, intraarterial, and intraperitoneal administration.

The Activin B compositions to be used in the therapy will be formulated and dosed in a fashion consistent with good medical practice taking into account the clinical condition of the individual patient, the cause of the erythropoietic condition in need of therapy, the site of delivery of the Activin B composition, the method of administration, the scheduling of administration, and other factors known to practitioners. The "effective amount" for purposes herein is thus determined by such considerations.

As a general proposition, the total pharmaceutically effective amount of the Activin B administered parenterally per dose will be in the range of about 1 μg/kg/day to 100 mg/kg/day of patient body weight, although, as noted above, this will be subject to a great deal of therapeutic discretion. The key factor in selecting an appropriate dose is the result obtained, as measured by increases in hemocrit values into the normal range or by other criteria as deemed appropriate by the practitioner.

The Activin B is also suitably administered by sustained release systems. Suitable examples of sustained release compositions include semi-permeable polymer matrices in the form of shaped articles, e.g., films, or microcapsules. Sustained release matrices include polylactides (U.S. Pat. No. 3,773,919, EP 58,481), copolymers of L-glutamic acid and gamma-ethyl-L-glutamate (U. Sidman et al., *Biopolymers*, 22, 547–556 (1983)), poly(2-hydroxyethyl methacrylate) (R. Langer et al., *J. Biomed. Mater. Res.*, 15: 167–277 (1981), and R. Langer, *Chem. Tech.*, 12: 98–105 (1982)), ethylene vinyl acetate (R. Langer et al., *Id.*) or poly-D-(-)-3-hydroxybutyric acid (EP 133,988). Sustained release Activin B compositions also include liposomally entrapped Activin B. Liposomes containing Activin B are prepared by methods known per se:

DE 3,218,121; Epstein et al., *Proc. Natl. Acad. Sci. U.S.A.*, 82: 3688–3692 (1985); Hwang et al., *Proc. Natl. Acad. Sci. U.S.A.*, 77: 4030–4034 (1980); EP 52,322; EP 36,676; EP 88,046; EP 143,949, EP 142,641; Japanese Pat. Appln. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal Activin B therapy.

For parenteral administration, the Activin B is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the Activin B uniformly and intimately with liquid carriers or finely divided solid carriers or both and then, if necessary, shaping the product into the desired formulation. Preferably the carrier is a parenteral carrier, more preferably a solution that is isotonic with the blood of the recipient. Examples of such carrier vehicles include water, saline, Ringer's solution, dextrose solution, and 5% human serum albumin. Non-aqueous vehicles such as fixed oils and ethyl oleate are also useful herein, as well as liposomes. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients. The Activin B is typically formulated in such vehicles at a concentration of about 0.1 mg/ml to 100 mg/ml at physiological pH.

Activin B for use in therapeutic administration must be sterile. Sterility is readily accomplished by sterile filtration through (e.g., 0.2 micron) membranes. Activin B ordinarily will be stored in unit or multi-dose containers, for example, sealed ampoules or vials, as an aqueous solution, as it is highly stable to thermal and oxidative denaturation. Lyophilized formulations for reconstitution are also acceptable.

Activin B therapy is suitably combined with other proposed or conventional erythropoietic therapies. Thus, for example, the Activin B in one embodiment can be combined with compounds that singly exhibit erythropoietic stimulatory effects, such as erythropoietin, testosterones, progenitor cell stimulators, insulin-like growth factor, prostaglandins, serotonin, cyclic AMP, prolactin, and triiodothyzonine, preferably erythropoietin. Also employable are compounds generally used to treat aplastic anemia, such as methenolene, stanozolol, and nandrolone; to treat iron-deficiency anemia, such as iron preparations; to treat malignant anemia, such as vitamin $B_{12}$ and/or folic acid; and to treat hemolytic anemia, such as adrenocortical steroids, e.g., corticoids. See, e.g., Resegotti et al., *Panminerva Medica*, 23: 243-248 (1981); Kurtz, *FEBS Letters*, 14a: 105-108 (1982); McGonigle et al., *Kidney Int.*, 25: 437-444 (1984)., and Pavlovic-Kantera et al., *Expt. Hematol.*, 8 (supp. 8) 283-291 (1980).

Compounds that enhance the effects of or synergize with erythropoietin are also useful as adjuvants herein, and include, e.g., adrenergic agonists, thyroid hormones, androgens, hepatic erythropoietic factors, erythrotropins, and erythrogenins. See, for example, Dunn, "Current Concepts in Erythropoiesis", John Wiley and Sons (Chichester, England, 1983); Weiland et al., *Blut*, 44 173-175 (1982); Kalmanti, *Kidney Int.*, 22: 383-391 (1982); Shahidi, *New Eng. J. Med.*, 289: 72-80 (1973); Fisher et al., *Steroids*, 30: 833-845 (1977); Urabe et al., *J. Exp. Med.*, 149: 1314-1325 (1979); Billat et al., *Expt. Hematol.*, 10: 133-140 (1982); Naughton et al., *Acta. Haemat.*, 69: 171-179 (1983); Congote et al. in Abstract 364, Proceedings 7th Intl. Cong. of Endocrinology (Quebec City, Quebec, July 1-7, 1984); Cingote, *Biochem. Biophys. Res. Comm.*, 115: 447-483 (1983); Congote, *Anal. Biochem.*, 140: 428-433 (1984); and Rothman et al., *J. Surg. Oncol.*, 20: 105-108 (1982).

The Activin B and cotreatment drug(s) are suitably delivered by separate or the same means, by separate or the same administration route, and at the same or at different times, depending, e.g., on dosing, the clinical condition of the patient, etc. It is not necessary that such cotreatment drugs be included in the Activin B compositions per se, although this will be convenient where such drugs are delivered by the same administration route.

When employed together with the Activin B, such agents typically are employed in lesser dosages than when used alone. A typical combined composition will contain the above-noted amount of Activin B and from about 0.1 (ca 7 units) to 100 (ca 7000 units) µg/kg body weight of erythropoietin in a suitable intravenous or intraperitoneal fluid such as lactated Ringer's solution.

In order to simplify the examples certain frequently occurring methods will be referenced by shorthand phrases.

"Plasmids" are designated by a low case p preceded and/or followed by an alphanumeric designation. The starting plasmids (and bacteriophages) herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 2 units of enzyme in about 20 µl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5′ phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., *Molecular Cloning: A Laboratory Manual,* (New York: Cold Spring Harbor Laboratories, 1982), pp. 133-134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9: 6103–6114 (1981), and D. Goeddel et al., *Nucleic Acids Res.* 8: 4057 (1980).

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, *J. Mol. Biol.* 98: 503–517 (1975), and hybridization as described by T. Maniatis et al., *Cell* 15: 687–701 (1978).

"Transformation" means introducing DNA into an organism so that the DNA is replicable, either as an extrachromosomal element or chromosomal integrant.

"Ligation" refers to the process of forming phosphodiester bonds between two double-stranded nucleic acid fragments (T. Maniatis et al., supra, p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., supra. p. 90, may be used.

"Oligonucleotides" are short-length, single- or double-stranded polydeoxynucleotides that are chemically synthesized by known methods and then purified on polyacrylamide gels.

"Site-specific mutagenesis" refers to mutagenesis of DNA that encodes an earlier prepared variant or a nonvariant version of the protein. Site-specific mutagenesis allows the production of variants through the use of specific oligonucleotide sequences that encode the DNA sequence of the desired mutation, as well as a sufficient number of adjacent nucleotides to provide a primer sequence of sufficient size and sequence complexity to form a stable duplex on both sides of the junction being traversed. Site-specific mutagenesis is well known in the art as exemplified by publications such as Adelman et al., *DNA,* 183 (1983), the disclosure of which is incorporated herein by reference.

The site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA,* Editor A. Walton, Elsevier, Amsterdam (1981), the disclosure of which is incorporated herein by reference. These phage are readily commercially available and their use is generally well known to those skilled in the art.

In general, site-directed mutagenesis is performed by first obtaining a single-stranded vector that includes within its sequence a DNA sequence that contains the relevant mutation. An oligonucleotide primer bearing the desired mutated sequence is prepared, generally synthetically, for example, by the method of Crea et al., *Proc. Natl. Acad. Sci.* (USA), 75: 5765 (1978). This primer is then annealed with the single-stranded original sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

The invention will be more fully understood by reference to the following examples. They should not, however, be construed as limiting the scope of the invention. All literature and patent citations are expressly incorporated by reference.

EXAMPLE I

Production of Human Activin B

Figure 9:
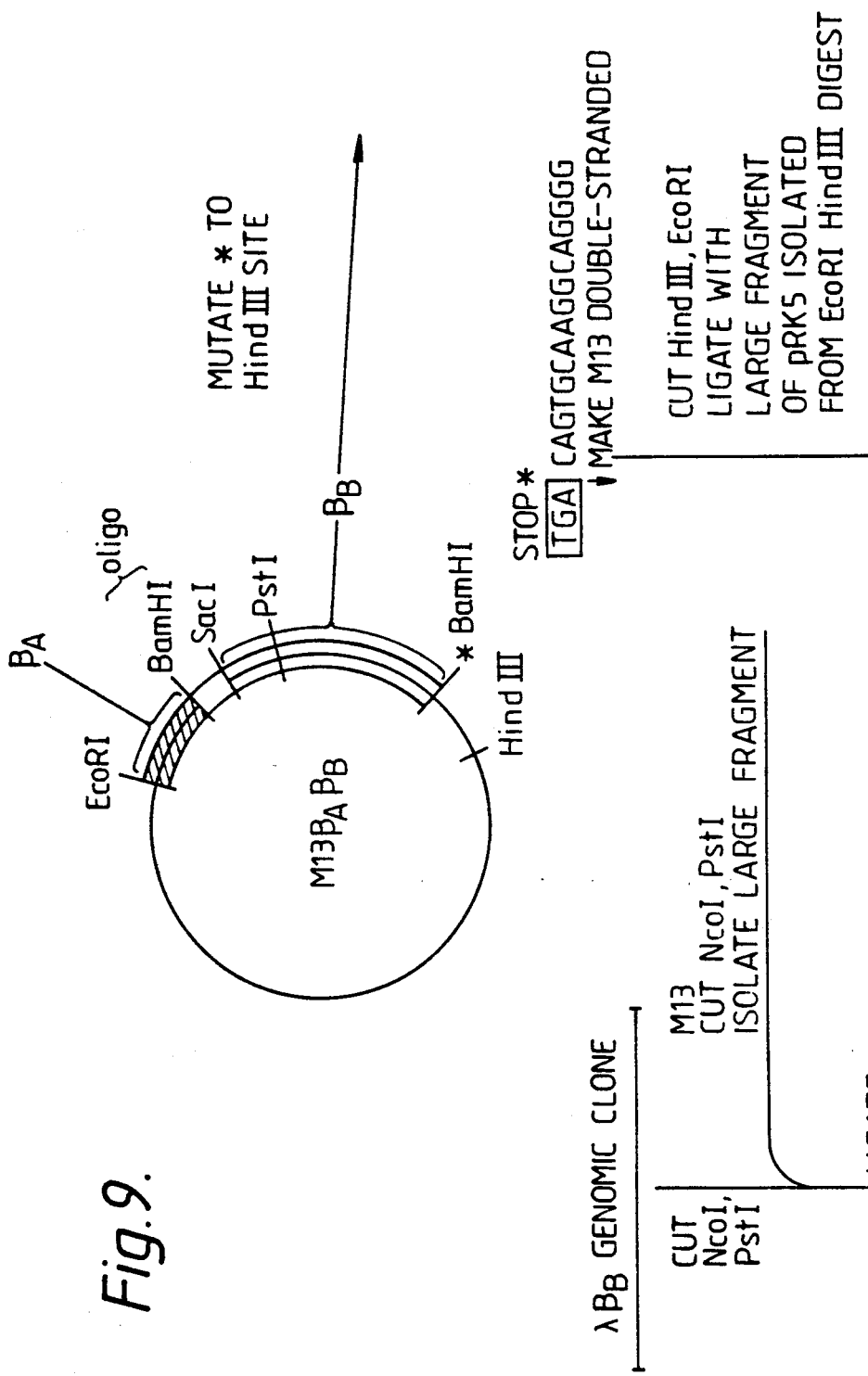
FIG. 9 depicts the construction of the final expression vector pRK$\beta_B$ used to transform mammalian host cells for expression of human Activin B.
Figure 9:
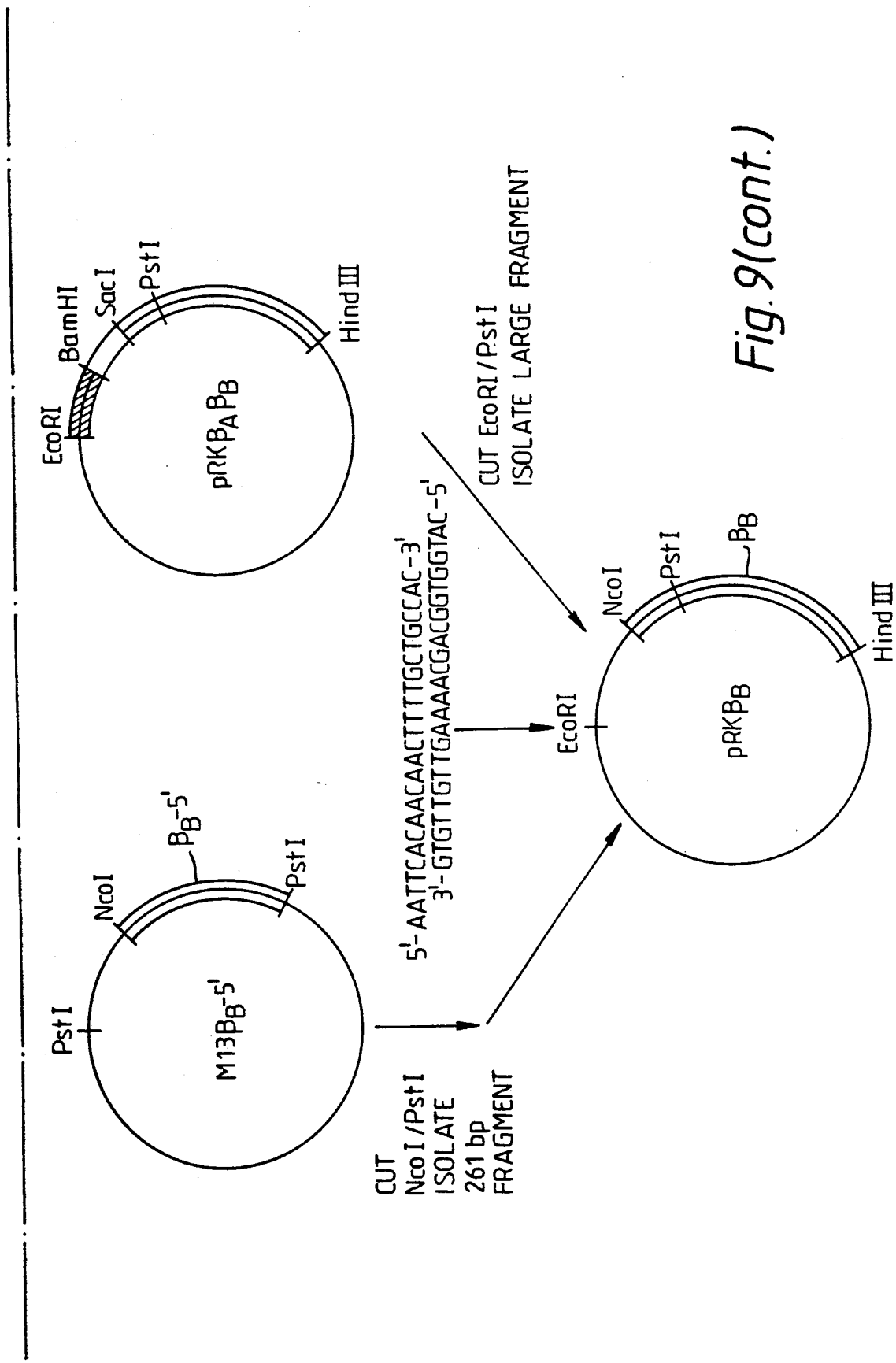

Activin B was recombinantly expressed in human kidney 293 cells transformed with an expression vector containing the gene coding for human Activin B. The expression vector, pRK$\beta_B$, was constructed, as shown in FIG. 9, from M13 containing a portion of the human inhibin $\beta_B$ genomic clone (M13$\beta_B$-5') and pRK$\beta_A\beta_B$ containing a fusion between the human inhibin $\beta_B$ partial-length cDNA sequence and the human inhibin $\beta_A$ cDNA 5'-end sequence. The construction of each of these intermediate vectors, and of the final expression plasmid, is described below in detail.

A. Construction of M13$\beta_B$-5'

A λgt10 library of human ovarian cDNA was prepared from 5 μg of ovarian mRNA using an oligo(dT)-primer that was 12–18 nucleotides in length and AMV reverse transcriptase. Both the Klenow fragment of DNA polymerase I and additional AMV reverse transcriptase were used to synthesize the second DNA strand using techniques well known in the art. The double-stranded cDNA (ds-cDNA) thus prepared was digested with S1 nuclease and treated with the Klenow fragment of DNA polymerase I. The now blunt-ended ds-cDNA was ligated to a double-stranded oligomer containing EcoRI adaptors and an internal XhoI site. The top strand is not phosphorylated and contains 16 nucleotides, whereas the bottom strand is phosphorylated and contains 12 nucleotides. The sequences are shown below:

5'-AATTCACTCGAGACGC-3'
3'-GTGAGCTCTGCG-5'

This ligation product was inserted into the EcoRI site of λgt10 as described by an instruction sheet included in a commercially available DNA packaging kit (Stratagene; San Diego, Calif., catalogue #GT-10), with the method also being described by Maniatis et al., supra.

This library was subjected to Southern analysis using as hybridization probes radiophosphate-labeled porcine inhibin cDNA encoding the α, $\beta_A$, and $\beta_B$ chains, described in EP 222,491, supra. The hybridization took place in the presence of 50% formamide, 6×SSC at 37°. The β chain clones were rare, with the $\beta_B$ clones being present at about one-third times the level of $\beta_A$ (1 and 3 out of about 1 million clones, respectively). None of the β chain clones were full length. They were supplemented with a primed cDNA library and assembled generally as described for the porcine cDNA in EP 222,491. The λ inserts were recovered by EcoRI digestion.

In detail, the lambda gt10 library yielded λHINβ$_A$-5$_s$ and -8$_s$ and 14. The EcoRI inserts of these phages were sequenced and their overlapping sequence is shown in FIG. 6A. The sequence on phage λ5$_s$ commences at nucleotide 207 of FIG. 6A. Two phages were employed to construct the full-length β$_A$-coding cDNA by ligating the 311 bp EcoRI-HindIII fragment (fragment 1) of λHINβ$_A$-5$_s$ to the 1101 bp HindIII-HpaI fragment (fragment 2) of λHINβ$_A$-14 and ligating this mixture in an EcoRI-SmaI-digested mp18 vector (Biolabs). Clones were selected and screened for the appropriate sized insert, and sequenced by the dideoxynucleotide chain termination method described by Sanger et al., *Proc. Natl. Acad. Sci.* (U.S.A.), 74: 5463-5467 (1977).

The nucleotide and deduced amino acid sequence for the human β$_A$ subunit is shown in FIGS. 6A, 6B, and 6C. The signal sequence is believed to be residues -28 through -1, with the precursor being 378 amino acids in length. The basic amino-terminal mature chain-processing site is indicated by a black bar, and a potential glycosylation site in the precursor is indicated by a cross-hatched bar above the sequence. Cysteine residues are shaded.

An mp18 vector containing the correct insert was primed with the lac 17-mer sequencing primer sold by Pharmacia, Inc. (TGACCGGCAGCAAAATC), DNA polymerase I, and the four dNTPs to render it double stranded, and thereafter digested with XbaI (which cleaves in the mp18 polylinker sequence) and EcoRI. The fragment containing the β$_A$ sequence was cloned into pRK5 (described below) that had been digested with EcoRI and XbaI, to obtain a 1423-bp fragment of β$_A$ in a plasmid designated pRKβ$_A$.

The lambda gt10 library also yielded λHINβ$_B$-3 and -16 and λHinβ$_B$2s. Phages λHINβ$_B$-3 and λHinβ$_B$2s were employed to construct a partial-length β$_B$-coding cDNA by ligating the 1400 bp NarI-BamHI fragment (fragment 3) of λHINβ$_B$-3 to the 437-bp EcoRI-NarI fragment (fragment 4) of λHinβ$_B$2s and ligating this fusion in a EcoRI-BamHI-digested mp18 vector (Biolabs). Clones were selected and screened for the appropriate sized insert of 1837 bases. Two clones were sequenced, and the β$_B$ cDNA sequence deduced from the clones was used to probe a human genomic library as described below.

Together, these two clones did not complete the full sequence for the β$_B$ subunit as shown in FIG. 7. This sequence was completed from the sequence of the genomic clone (see below). The sequence at the end of the EcoRI-NarI fragment of the cDNA was not in frame and needed to be confirmed by genomic sequences, as cDNA 5'-end artifacts are common.

A human genomic DNA library in lambda Charon 4A (Lawn. R. M. et al., *Cell*, 15: 1157-1174 (1978)) was screened using the method of Maniatis et al., supra. Southern hybridization was employed (Southern, *J. Mol. Biol.*, 98: 503-517 (1975)) using $^{32}$-P-labeled human inhibin β$_B$ cDNA as the probe (a 65-mer spanning from nucleotides 246 to 310 of FIG. 7). The hybridization was performed at 37° C. in 6×SSC, 0.5% NP-40, 6 mM EDTA, 1×Denhardt's solution, and 50 μg/ml salmon sperm DNA. Several washes were performed at room temperature in 6×SSC before autoradiography. DNA from one lambda phage hybridized with the probe. DNA from this phage was digested with PstI and subcloned into M13 as a pool. This pool was screened with the 65-mer (see above).

A hybridizing M13 clone, M13β$_B$-5', was isolated and sequenced by the method of Sanger et al., supra. This sequence was collated with the previously determined partial β$_B$ sequence. Both sequences overlapped at the PstI site, and gave a sequence that predicted an open reading frame, beginning with an initiator methionine and followed by a signal sequence. A discrepancy occurred between the two sequences at nucleotide 189 (FIG. 7)—a T in the genomic sequence and a G in the cDNA sequence. This change alters the amino acid from a serine to an alanine residue.

B. Construction of pRKβ$_A$β$_B$

B.1. Construction of pF8CIS

The initial three-part construction of the starting plasmid pF8CIS is described below and shown in FIG. 1.

1) The ampicillin resistance marker and replication origin of the final vector was derived from the starting plasmid pUC13pML, a variant of the plasmid pML (Lusky, M. and Botchen, M., *Nature*, 293: 79 [1981]). pUC13pML was constructed by transferring the polylinker of pUC13 (Vieira, J. and Messing, J., *Gene*, 19:259 (1982)) to the EcoRI and HindIII sites of pML. A second starting plasmid pUC8-CMV was the source of the CMV enhancer, promoter and splice donor sequence. pUC8-CMV was constructed by inserting approximately 800 nucleotides for the CMV enhancer, promoter and splice donor sequence into the blunted PstI and SphI sites of pUC8. Vieira, J, and Messing, J., supra. Synthetic BamHI-HindIII linkers (commercially available from New England Biolabs) were ligated to the cohesive BamHI end creating a HindIII site. Following this ligation a HindIII-HincII digest was performed. This digest yielded a fragment of approximately 800 bp that contained the CMV enhancer, promoter and splice donor site. Following gel isolation this 800-bp fragment was ligated to a 2900-bp piece of pUC13pML. The fragment required for the construction of pF8CIS was obtained by digestion of the above intermediate plasmid with SalI and HindIII. This 3123 bp piece contained the resistance marker for ampicillin, the origin of replication from pUC13pML, and the control sequences for the CMV, including the enhancer, promoter, and splice donor site.

Figure 1B:
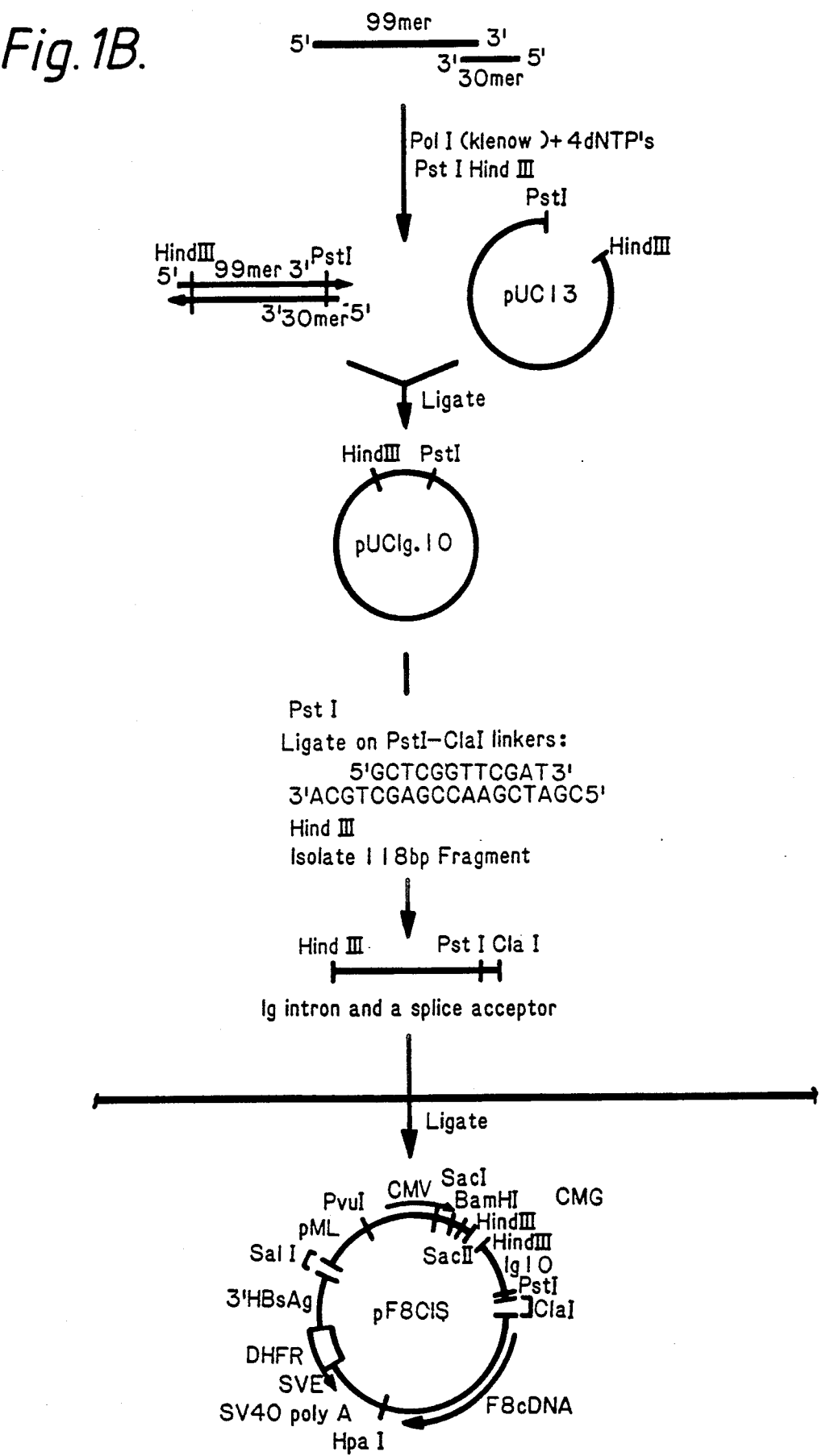
Figure 1C:
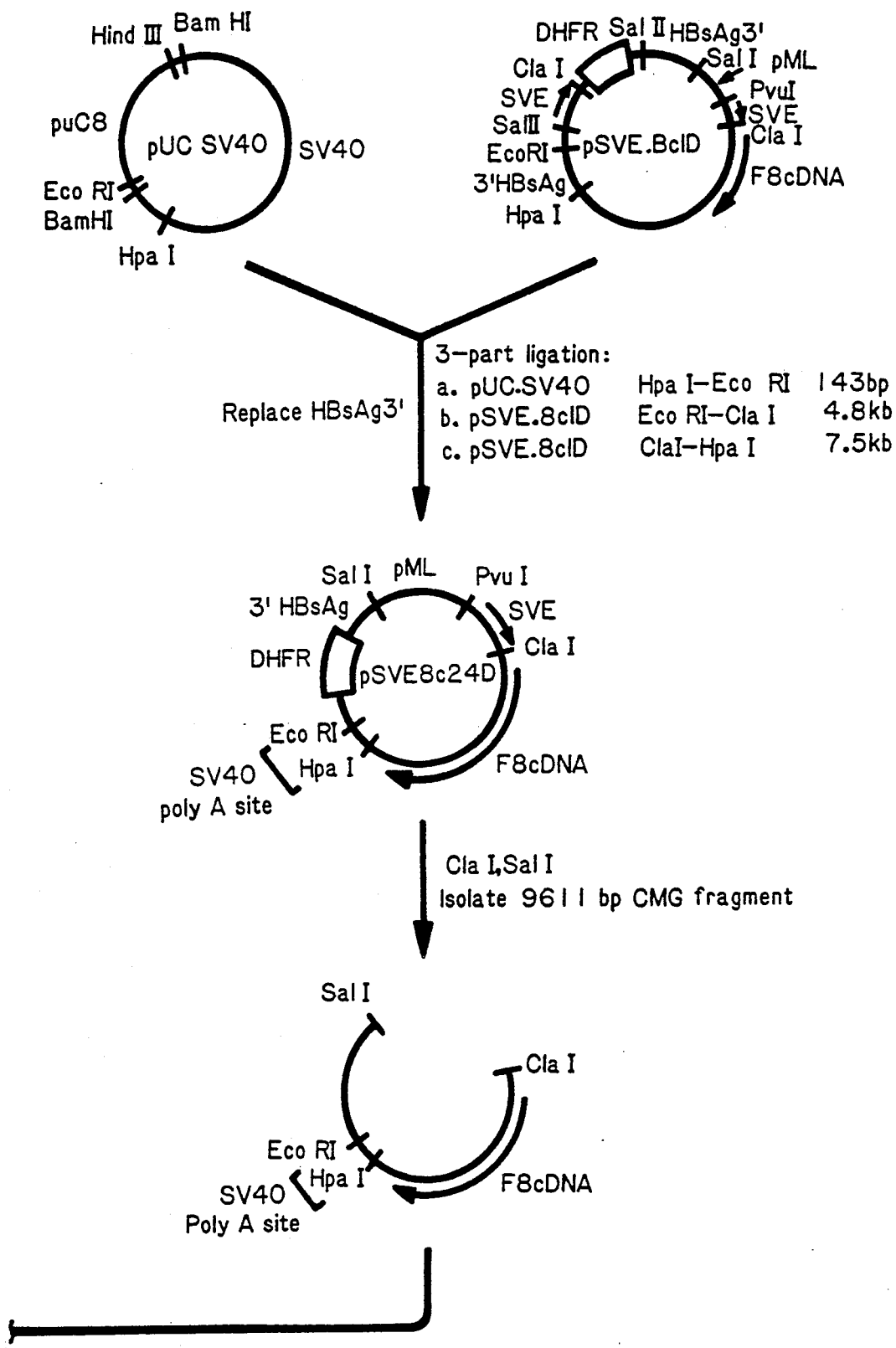

2) The Ig variable region intron and splice acceptor sequence was constructed using a synthetic oligomer as shown in the central portion of FIG. 1. A 99 mer and a 30 mer were chemically synthesized having the following sequence for the IgG intron and splice acceptor site (Bothwell et al., *Nature*, 290:65-67 [1981]):

1   5'   AGTAGCAAGCTTGACGTGTG-
         GCAGGCTTGA. . .
31            GATCTGGCCATACACTTGAGT-
         GACAATGA. . .
60  CATCCACTTTGCCTTTCTCTCCACAGGT.

88 GTCCACTCCCAG 3'
1      3'      CAGGTGAGGGTGCAGCTT-
         GACGTCGTCGGA 5'

DNA polymerase I (Klenow fragment) filled in the synthetic piece and created a double-stranded fragment. Wartell, R. M. and W. S. Reznikoff, *Gene*, 9: 307 (1980). This was followed by a double digest of PstI and HindIII. This synthetic linker was cloned into pUC13 (Veira and Messing, supra) at the PstI and HindIII sites. The clone containing the synthetic oligonucleotide, labeled pUCIg.10, was digested with PstI. A ClaI site was added to this fragment by use of a PstI-ClaI linker. Following digestion with HindIII a 118-bp piece containing part of the Ig intron and the Ig variable region splice acceptor was gel isolated.

3) The third part of the construction scheme replaced the hepatitis surface antigen 3' end with the polyadenylation site and transcription termination site of the early region of SV40. A vector, pUC.SV40, containing the SV40 sequences was inserted into pUC8 at the BamHI site described by Vieira and Messing, supra. pUC.SV40 was then digested with EcoRI and HpaI. A 143-bp fragment containing the SV40 polyadenylation sequence was gel isolated from this digest. Two additional fragments were gel isolated following digestion of pSVE.8clD. (European Pat. Pub. No. 160,457). The 4.8 kb fragment generated by EcoRI and ClaI digestion contains the SV40-DHFR transcription unit, the origin of replication of pML, and the ampicillin resistance marker. The 7.5-kb fragment produced following digestion with ClaI and HpaI contains the cDNA for Factor VIII. A three-part ligation yielded pSVE.8c24D. This intermediate plasmid was digested by ClaI and SalI to give a 9611-bp fragment containing the cDNA for Factor VIII with an SV40 poly A site followed by the SV40 DHFR transcription unit.

The final three-part ligation to yield pF8CIS used: a) the 3123-bp SalI-HindIII fragment containing the origin of replication, the ampicillin resistance marker, and the CMV enhancer, promoter, and splice donor site; b) the 118 bp HindIII-ClaI fragment containing the Ig intron and splice acceptor site; and c) a 9611 bp ClaI-SalI fragment containing the cDNA for Factor VIII, the SV40 polyadenylation site, and the SV40 DHFR transcription unit.

B.2. Construction of pCIS2.8c28D pCIS2.8c28D comprises a 90kd subunit of Factor VIII joined to a 73kd subunit of Factor VIII. The 90kd subunit comprises amino acids 1 through 740 and the 73kd subunit amino acids 1690 through 2332. This construct was prepared by a three-part ligation of the following fragments: a) the 12617-bp ClaI-SstII fragment of pF8CIS (isolated from a dam-strain and BAP treated); b) the 216-bp SstII-PstI fragment of pF8CIS; and c) a short PstI-ClaI synthetic oligonucleotide that was kinased (see FIG. 2, where an asterisk indicates the changed nucleotide).

Figure 2:
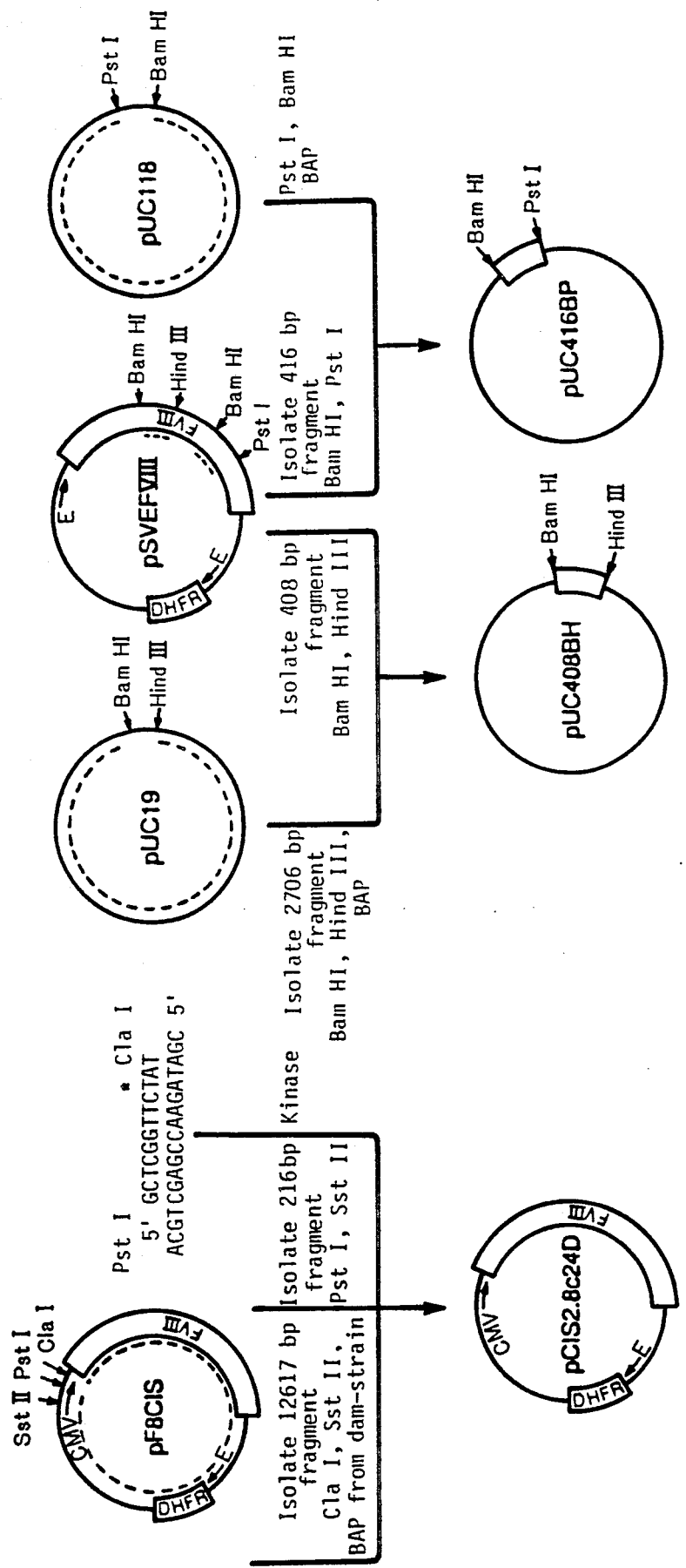
FIG. 2 depicts the construction of the intermediate vector pCIS2.8c24D for Factor VIII in which the ClaI site is not effected by dam methylation. Also shown is the subcloning of 408 and 416 bp fragments of the Factor VIII coding region for construction of a fusion plasmid.

FIG. 2 also shows the subcloning of the 408 bp BamHI-HindIII and the 416 bp BamHI-PstI fragments of pSVEFVIIII (European Pat. Publ. No. 160,457) containing the 5' and 3' DNA regions of Factor VIII to be fused to make pCIS2.8c28D.

Figure 3:
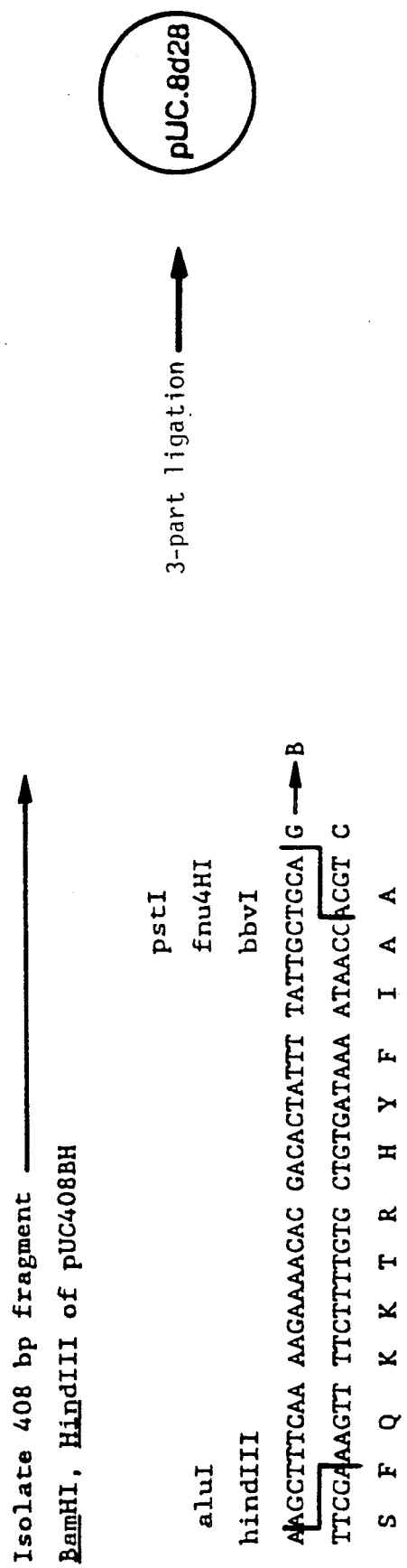
FIG. 3 depicts the construction of the intermediate plasmid pUC.8d28 containing the fusion region of a Factor VIII variant in a pUC vector.

FIG. 3 shows the three-part ligation used to construct the fusion region of pCIS2.8c28D. Two different fragments, A and B, were cloned into the BamHI-PstI fragment from pUC118 treated with bacterial alkaline phosphatase. (pUC118 is described by Vieira and Messing, *Meth. Enzym.*, 153: 3–11 (1987). Briefly, it is a 3.2 kb plasmid with ampicillin resistance and an M13 region and a sequence encoding the lac Z peptide containing unique restriction sites for cloning.) The A fragment was the 408-bp BamHI-HindIII fragment of pUC408BH (described above and in FIG. 2), and the B fragment was a HindIII-PstI oligonucleotide. The double-stranded oligonucleotide is shown in FIG. 3. While complete DNA sequence at the terminal restriction sites is given in FIG. 3, the actual oligonucleotide does not include the bases delineated by the lines at the restriction sites. This oligonucleotide was used without kinasing to prevent its polymerization during ligation.

After ligation of the A and B fragments into the vector as shown in FIG. 3, the expected junction sequences were confirmed by DNA sequencing of the regions encompassed by the nucleotides.

Figure 4:
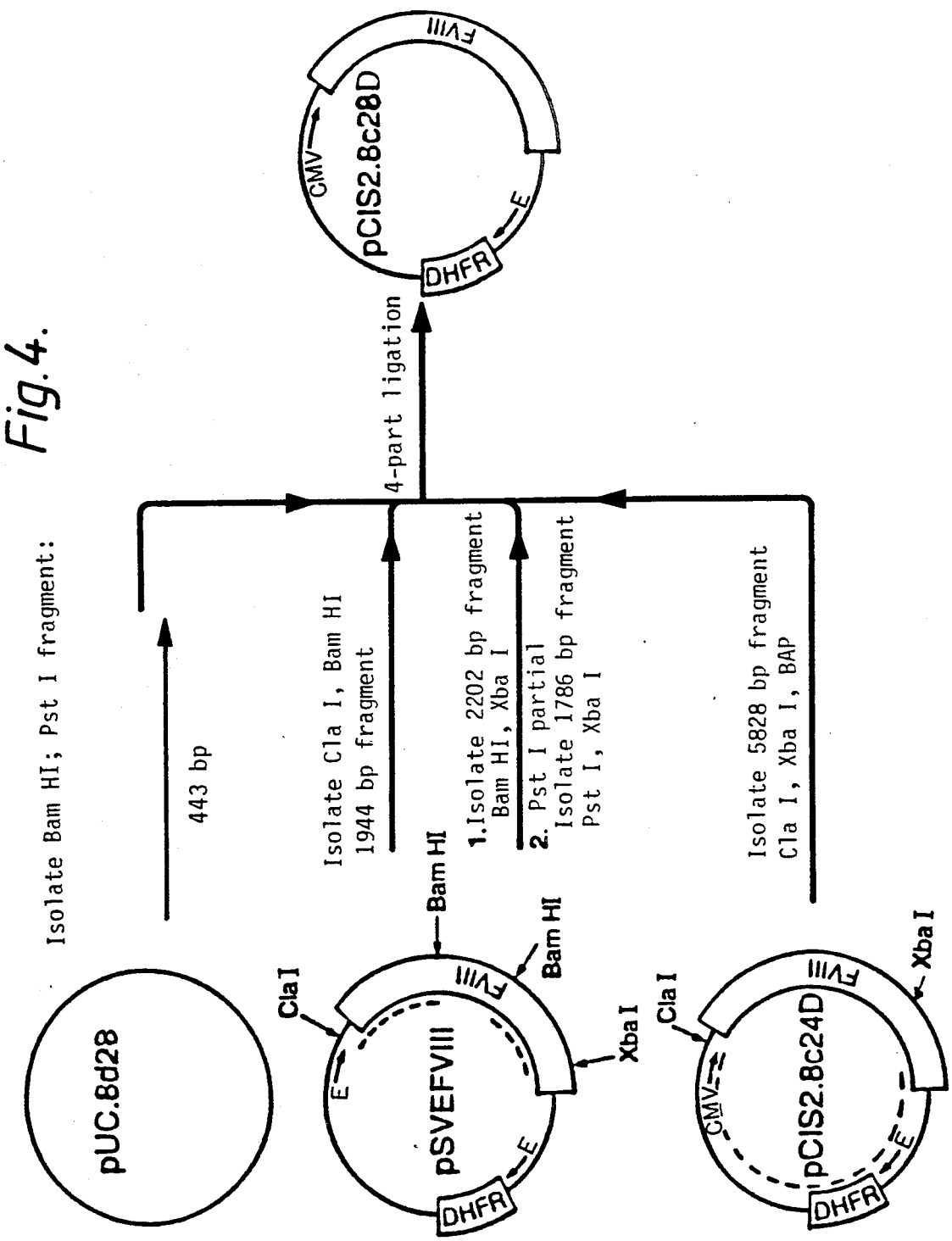
FIG. 4 depicts the construction of the intermediate expression vector designated pCIS2.8c28D that encodes a Factor VIII variant protein.

The resulting plasmid, pCIS2.8c28D, was constructed as shown in FIG. 4, with a four-part ligation. The fusion plasmid from FIG. 3 was cut with BamHI and PstI and the 443 bp fragment isolated. The remaining three fragments of the four-part ligation were: 1) 1944 bp ClaI-BamHI of pSVEFVIII (European Pat. Publ. No. 160,457); 2) a 2202 bp BamHI-XbaI fragment of pSVEFVIII, which was further partially digested with PstI and the 1786 bp PstI-XbaI fragment was isolated, and 3) the 5828 bp XbaI-ClaI BAP fragment of pCIS2.8c24D from FIG. 3. The translated DNA sequence of the resultant variant in the exact fusion junction region of pCIS2.8c28D was determined and correlates with the sequence shown in FIG. 3.

B.3. Construction of pRK5

Figure 5:
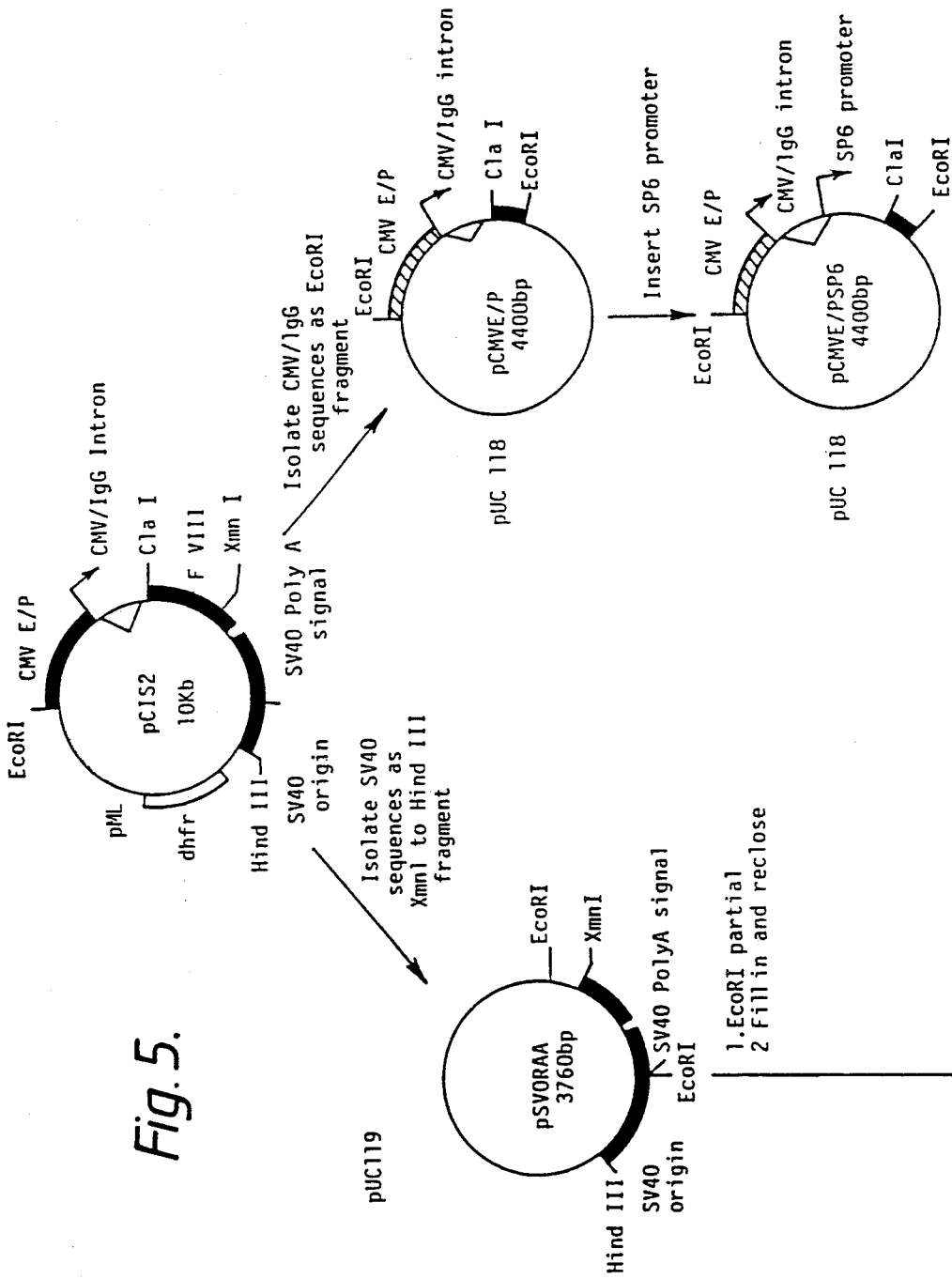
FIG. 5 depicts the construction of the intermediate expression vector pRK from pCIS2.
Figure 5:
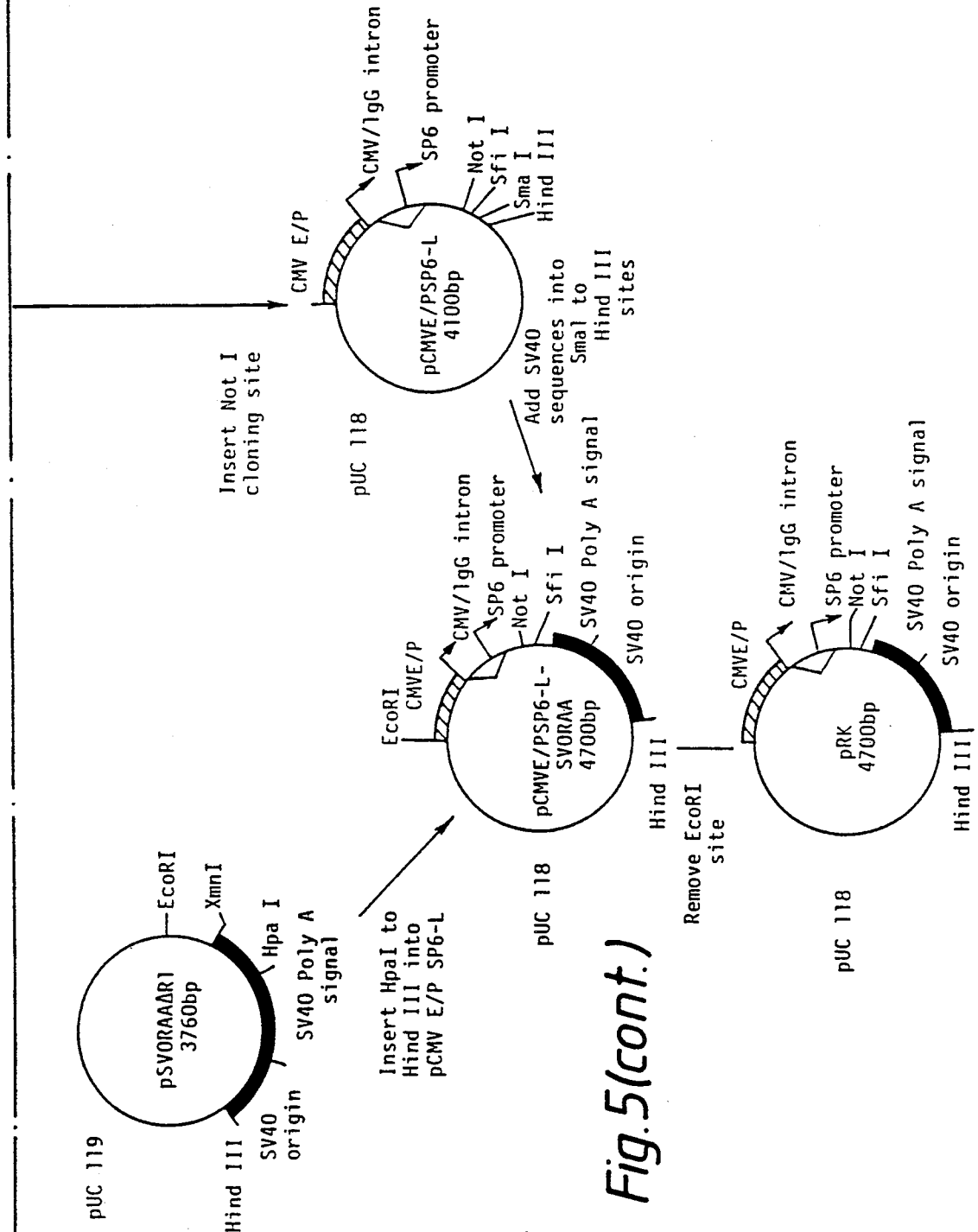

The construction of pRK5 is depicted in FIG. 5. The starting plasmid for construction of pRK5 was pCIS2.8c28D. The base numbers in paragraphs 1 through 6 refer to pCIS2.8c28D with base one of the first T of the EcoRI site preceding the CMV promoter. The cytomegalovirus early promoter and intron and the SV40 origin and polyA signal were placed on separate plasmids.

1. The cytomegalovirus early promoter was cloned as an EcoRI fragment from pCIS2.8c28D (9999-1201) into the EcoRI site of pUC118 described above. Twelve colonies were picked and screened for the orientation in which single-stranded DNA made from pUC118 would allow for the sequencing from the EcoRI site at 1201 to the EcoRI site at 9999. This clone was named pCMVE/P.

2. Single-stranded DNA was made from pCMVE/P in order to insert an SP6 (Green, MR et al., *Cell*, 32: 681–694 [1983]) promoter by site-directed mutagenesis. A synthetic 110 mer that contained the sequences from −69 to +5 of SP6 promoter (see *Nucleic Acids Res.*, 12: 7041 [1984], FIG. 1) were used along with 18-bp fragments on either end of the oligomer corresponding to the CMVE/P sequences. Mutagenesis was done by standard techniques and screened using a labeled 110 mer at high and low stringency. Six potential clones were selected and sequenced. A positive clone was identified and labeled pCMVE/PSP6.

3. The SP6 promoter was checked and shown to be active, for example, by adding SP6 RNA polymerase and checking for RNA of the appropriate size.

4. A Cla-NotI-Sma adapter was synthesized to encompass the location from the ClaI site (912) to the SmaI site of pUC118 in pCMVE/P (step 1) and pCMVE/PSP6 (step 2). This adapter was ligated into the ClaI-SmaI site of pUC118 and screened for the correct clones. The linker was sequenced in both and clones were labeled pCMVE/PSP6-L and pCMVE/P-L.

5. pCMVE/PSP6-L was cut with SmaI (at linker/-pUC118 junction) and HindIII (in pUC118). A HpaI (5573)-to-HindIII (6136) fragment from pSVORAA-ΔRI 11, described below, was inserted into SmaI-HindIII of pCMVE/PSP6-L. This ligation was screened and a clone was isolated and named pCMVE/PSP6-L-SVORAAΔRI.

a) The SV40 origin and polyA signal was isolated as the XmnI (5475)-HindIII (6136) fragment from pCIS2.8c28D and cloned into the HindIII to SmaI sites of pUC119 (described in Vieira and Messing, op. cit.). This clone was named pSVORAA.

b) The EcoRI site at 5716 was removed by partial digestion with EcoRI and filling in with Klenow. The colonies obtained from self-ligation after fill-in were screened and the correct clone was isolated and named pSVORAAΔRI 11. The deleted EcoRI site was checked by sequencing and shown to be correct.

c) The HpaI (5573) to HindIII (6136) fragment of pSVORAAΔRI 11 was isolated and inserted into pCMVE/PSP6-L (see 4 above).

6. pCMVE/PSP6-L-SVORAAΔBI (step 5) was cut with EcoRI at 9999, blunted and self-ligated. A clone without an EcoRI site was identified and named pRK.

7. pRK was cut with SmaI and BamHI. This was filled in with Klenow and religated. The colonies were screened. A positive clone was identified and named pRKΔBam/Sma3.

8. The HindIII site of pRKΔBam/Sma3 was converted to a HpaI site using a converter. (A converter is a piece of DNA used to change one restriction site to another. In this case one end would be complementary to a HindIII sticky end and the other end would have a recognition site for HpaI.) A positive clone was identified and named pRKΔBam/Sma, HIII-HpaI 1.

9. pRKΔBam/Sma, HIII-HpaI 1 was cut with PstI and NotI and an EcoRI-HindIII linker and HindIII-EcoRI linker were ligated in. Clones for each linker were found. However, it was also determined that too many of the HpaI converters had gone in (two or more converters generate a PvuII site). Therefore, these clones had to be cut with HpaI and self-ligated.

10. RI-HIII clone 3 and HIII-RI clone 5 were cut with HpaI, diluted, and self-ligated. Positives were identified. The RI-HIII clone was named pRK5.

B.4 Construction of M13β_Aβ_B

Figure 8:
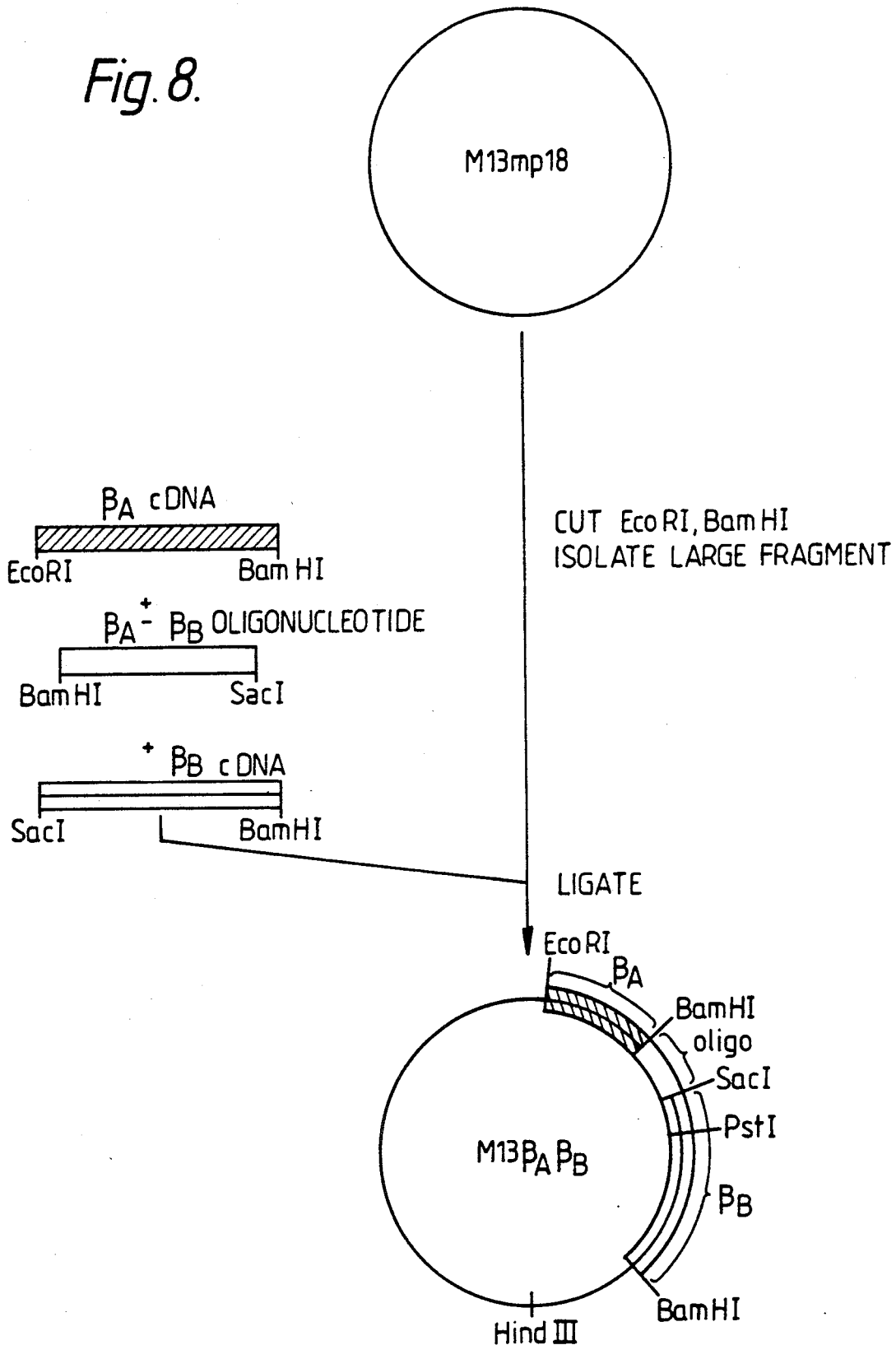
FIG. 8 depicts the construction of the intermediate expression vector M13$\beta_A\beta_B$ from M13mp18.

The construction is illustrated in FIG. 8. The bacteriophage M13mp18 (Messing et al., supra) was digested with EcoRI and BamHI. Meanwhile, the fragment of β_A contained in pRKβ_A described above was cleaved with EcoRI and BamHI to obtain a 120-bp fragment. The 1837-bp fragment of β_B described above was digested with SacI and BamHI to yield a 1603-bp fragment. These two β subunit fragments were ligated with the EcoRI-BamHI-digested M13mp18 vector and the following oligonucleotide sequence to yield a β_Aβ_B fusion, with the β_A fragment at the 5' end. (The oligonucleotide has a 5' site and a 3' SacI site, thus joining the two fragments together to produce a β_Aβ_B fusion.) The sequence for this oligonucleotide, derived from 310–341 of β_A (FIG. 6A) and 210–244 of β_B (FIG. 7), is shown below:

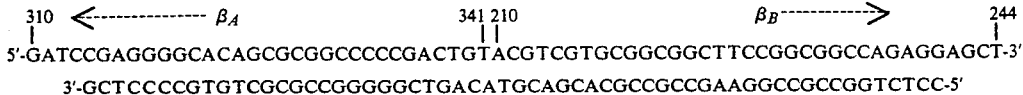

ARI 11, described below, was inserted into SmaI-HindIII of pCMVE/PSP6-L.

B.5 Construction of pRKβ_Aβ_B

The construction of this plasmid is shown in FIG. 9, where the stippled area represents the β_A-encoding region, the open bar area is the oligonucleotide linker, and the open bar area with a middle line represents the β_B-encoding region. The M13β_Aβ_B has an untranslated region at its 3' end between the asterisk in the figure and the BamHI site. This region where the asterisk is located was mutated to form a HindIII site by using site-directed mutagenesis to make the mutation.

Mutagenesis on the above template was carried out using the oligodeoxyribonucleotide, 5'-TGACAGTGCAAGGCAGGGG-3', which contains a stop codon and a HindIII site, essentially as described by Zoller et al., Meth. Enzymol., 100: 468 (1983). Mutations were verified by DNA sequencing directly on the single-stranded M13 DNA using the dideoxynucleotide chain termination method (Sanger et al., Proc. Natl. Acad. Sci. (U.S.A.) 74: 5463 (1977)).

The resulting M13 phage was made double-stranded by the 17-mer described above, DNA Polymerase I, and four dNTPs. The resulting double-stranded phage was digested with HindIII and EcoRI and ligated into pRK5 digested with EcoRI and HindIII. The result is pRKβ_Aβ_B.

Plasmids containing the β_B subunit may also be obtained by simply cloning the β_B sequence shown in FIG. 7 into an appropriate plasmid for expression, without having to digest out the β_A sequence.

C. Construction of pRKβ_B

FIG. 9 depicts the construction of pRKβ_B. M13β_B-5' was digested with NcoI and PstI and the resulting 261-bp fragment was isolated. Plasmid pRKβ_Aβ_B was also digested with EcoRI and PstI and the large fragment was isolated. A synthetic oligonucleotide was prepared having the sequence

These three fragments were ligated to form the plasmid pRKβ_B containing the full β_B subunit in a pRK5 vector. The recombinant clones were screened by restriction enzyme digestion to determine the proper orientation of the β_B genes following the CMV promoter, and the sequence was checked.

D. Expression of Human Activin B

Human embryonic kidney cells transformed with adenovirus E1a dn E1b (293s) have been described by Graham et al., J. Gen. Virol., 36: 59–73 (1977). These cells were transfected with the above-described expression vector pRKβ_B showing the proper orientation by the calcium phosphate method of Gorman, in DNA Cloning, D. M. Glover, ed. (IRC Press, Oxford. 1985), vol. 2, pp. 143–190. Seventy-two hours later, cells were subcultured into 800 μg/ml G418 for selection of stable clones. A total of twenty clones were expanded into 12-well plates and supernatants were tested for activity in the K562 assay as described below.

The biological assay for erythropoietin activity was performed using the human K-562 cell line described by Lozzio et al., *Blood*, 45: 321-334 (1975). K562 cells were cultured in RPMI, 10% fetal bovine serum in the absence or presence (at varying concentrations) of human Activin B produced as described above. After four days, hemoglobin content of the cells was determined photometrically as described by Schmidt et al., *Cell.* 46: 41-51 (1986). Briefly, the cells were washed twice with phosphate-buffered saline and lysed in 50 μl water for 15 minutes at room temperature. Debris was removed by centrifugation and 40 μl of the supernatant was transferred to a 96-well microtiter plate. To each well was added 200 μl of a reaction mixture consisting of citrate-phosphate buffer containing 0.5 mg/ml o-phenylenediamine plus 0.03% hydrogen peroxide. The reaction was incubated for 15 minutes in the dark and quenched with 50 μl 2.5M sulfuric acid. Optical density was measured at 490 nm.

Figure 10:
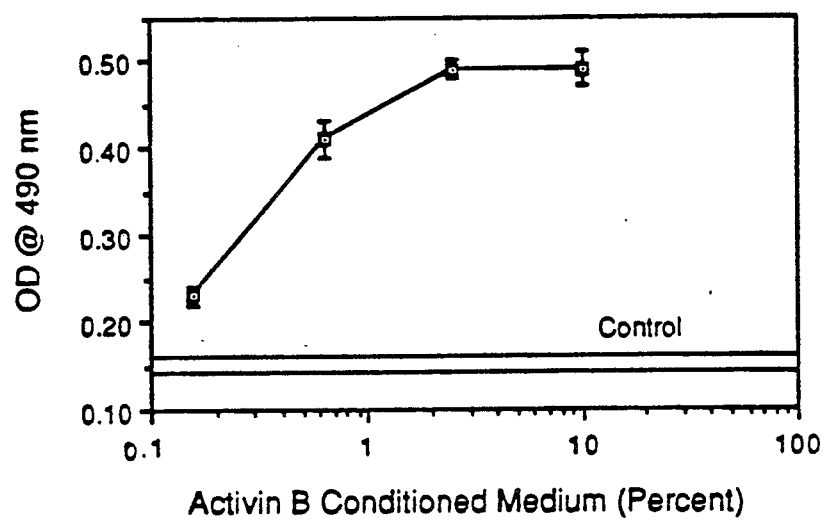
FIG. 10 depicts a graph of optical densities at 490 nm versus concentration of Activin B, where optical density signifies cell assay for hemoglobin content using K562 cells.

The results are shown in FIG. 10, where the various concentrations of human Activin B are provided. Each optical density point on the graph is the mean ± standard deviation of triplicate values from a representative experiment. The open bar represents mean ± standard deviation for controls.

The expression of Activin B from the host cells transformed with pRK$\beta_A\beta_B$ worked as well as the expression from host cells transformed with pRK$\beta_B$.

E. Purification of Human Activin B

An initial volume (40 liters) of the tissue culture fluid of the best clone was concentrated using a pellicon concentrator (final volume 560 ml). The concentrate was diafiltered in 25 mM 2-(N-morpholino)ethane sulfonic acid (MES), pH 6.5, 6M urea and then applied to a sulfopropyl-Sepharose Fast Flow column (5×13 cm) equilibrated with a buffer of 25 mM MES, pH 6.5, 6M urea.

The active fraction from the sulfopropyl-Sepharose column was adjusted with solid sodium chloride to 0.8M NaCl and loaded onto a phenyl sepharose (CL-4B) column (2.5×8.0 cm) equilibrated with 25 mM 3-[N-morpholino]propane sulfonic acid (MOPS), pH 7.0, 6M urea, 0.8M NaCl. The column, operating at a flow rate of 3.5 ml/min., was washed sequentially with at least two column volumes of equilibration buffer and 25 mM MOPS, pH 7.0, 6M urea. Activin B was eluted using up to 2.5 column volumes of a mixture of 40% ethanol (Baker 9401-03) and 60% 25 mM MOPS, pH 7, 6M urea.

The Activin-B-containing fraction was loaded onto a Sephacryl-S-300 HR column (1.5×44 cm) equilibrated in either 25 mM MOPS, pH 7, 6M urea; or 1M acetic acid; or 1M acetic acid, 7.1M urea, at a flow rate of 0.7 ml/min. The Activin-B-containing fractions were pooled and injected onto either a C18 RP-HPLC or C4 RP-HPLC column (0.46×25 cm) at a flow rate of 1 ml/min. Activin B was eluted from the column using a gradient mixture between water and acetonitrile, both containing 0.1% trifluoroacetic acid.

SDS-PAGE analysis was used to locate the elution position of Activin B in the RP-HPLC fractions, and the appropriate fractions containing Activin B were subjected to the assay described below. SDS-PAGE conducted under non-reducing conditions using a silver stain revealed a major band that corresponded to the molecular weight of Activin B and a minor band of higher molecular weight. It is estimated that the purity of the Activin B is at least 80% by weight, with the remaining polypeptide(s) being of human origin.

EXAMPLE II

Use of Human Activin B

Groups of five male mice (6-8 weeks old) are used. Mouse Friend leukemia cells, F5-5, serially subcultured in mouse ascites, are transplanted into the abdomen of each mouse ($2 \times 10^6$ cells for each). The Activin B from Example I is dissolved in sterile saline at physiological pH to give a parenteral injection of about 5000 units per ml. This preparation is injected abdominally or intravenously into the mice in each group daily for three days from the next day after the leukemia cells are transplanted. Blood samples are collected from the caudal vein 14 and 21 days after transplantation, and the hematocrit values are measured after centrifugation at 12,000 rpm for five minutes. The control group is injected with saline rather than Activin B preparation. The test groups that are treated intravenously and abdominally with the Activin B preparation have increased hematocrit values over the control group after both 14 and 21 days, and have almost the same hematocrit values as those of the mice before transplantation of the leukemia cells.

What is claimed is:

1. A human Activin B composition, which composition has the purity (at least about 90% by weight) of Activin B produced by the method comprising:
    (a) diafiltering a fluid containing unpurified Activin B in 25 mM 2-(N-morpholino)ethane sulfonic acid (MES), pH 6.5, 6M urea;
    (b) applying the diafiltrate to a sulfopropyl-Sepharose Fast Flow column equilibrated with a buffer of 25 mM MES, pH 6.5, 6M urea;
    (c) adjusting the Activin-B-containing fraction from the sulfopropyl-Sepharose column with sodium chloride to 0.8M NaCl;
    (d) applying the NaCl-adjusted fraction to a phenyl sepharose column equilibrated with an equilibration buffer of 25 mM 3-[N-morpholino]propane sulfonic acid (MOPS), pH 7.0, 6M urea, 0.8M NaCl:
    (e) washing the column of step (d) sequentially with at least two column volumes of the equilibration buffer and 25 mM MOPS, pH 7.0, 6M urea;
    (f) eluting Activin B from the phenyl sepharose column with up to 2.5 column volumes of a mixture of about 40% ethanol and 60% 25 mM MOPS, pH 7, 6M urea;
    (g) applying the Activin-B-containing fraction from the phenyl sepharose column to a Sephacryl-S-300 HR column equilibrated in either (a) 25 mM MOPS, pH 7, 6M urea, or (b) 1M acetic acid, 7.1M urea, and eluting the Activin-B containing fractions from the HR column and pooling them;
    (h) applying the pooled fractions to a RP-HPLC column; and
    (i) eluting the Activin-B-containing fractions from the RP-HPLC column using a gradient mixture between water and acetonitrile, both containing 0.1% trifluoroacetic acid.

2. The composition of claim 1 wherein the purity of the Activin B is at least about 95% by weight.

3. The composition of claim 1 that is a pharmaceutical composition useful for erythropoietin therapy further comprising a pharmaceutically acceptable carrier.

4. The composition of claim 3 wherein the carrier is parenteral.

5. The composition of claim 3 further comprising a compound selected from the group consisting of an iron preparation, vitamin $B_{12}$, folic acid, an adrenocortical steroid, an erythropoietin, a testosterone, a progenitor cell stimulator, insulin-like growth factor, a prostaglandin, serotonin, cyclic AMP, prolactin, triiodothyzonine, methenolene, stanozolol, nandrolone, an adrenergic agonist, a thyroid hormone, an androgen, a hepatic etythropoietic factor, an erythrotropin, and an erythrogenin.

6. The composition of claim 5 wherein the compound is erythropoietin.

* * * * *

UNITED STATES PATENT AND TRADEMARK OFFICE
CERTIFICATE OF CORRECTION

PATENT NO. : 5,071,834
DATED : December 10, 1991
INVENTOR(S) : Louis E. Burton, Anthony J. Mason, Charles H. Schmelzer It is certified that error appears in the above-identified patent and that said Letters Patent is hereby corrected as shown below:

On the title page, please add:  Related U.S. Application Data
[63] Continuation of Ser. No. 07/245,845,
Sep. 16, 1988, abandoned.

Column 1, line 2, after the title, insert:

"This is a continuation of Ser. No. 07/245,845, filed September 16, 1988, now abandoned."

Signed and Sealed this

Thirteenth Day of April, 1993

*Attest:*

STEPHEN G. KUNIN

*Attesting Officer*    *Acting Commissioner of Patents and Trademarks*